United States Patent [19]
Yamamoto

[11] Patent Number: 5,752,833
[45] Date of Patent: May 19, 1998

[54] METHOD FOR REPAIRING DENTAL ENAMEL

[75] Inventor: Masao Yamamoto, Tama, Japan

[73] Assignee: Scalar Co., Tokyo, Japan

[21] Appl. No.: 634,852

[22] Filed: Apr. 19, 1996

[51] Int. Cl.⁶ .................................................. A61C 5/04
[52] U.S. Cl. .................... 433/226; 433/215; 433/228.1
[58] Field of Search ................................. 433/215, 222, 433/226, 228.1

[56] References Cited

U.S. PATENT DOCUMENTS

| 5,194,005 | 3/1993 | Levy | 433/215 |
| 5,554,029 | 9/1996 | Kowalyk et al. | 433/226 |

*Primary Examiner*—John J. Wilson
*Attorney, Agent, or Firm*—Nikaido, Marmelstein, Murray & Oram LLP

[57] ABSTRACT

A method for effectively repairing damage to dental enamel. In a repairing process, employed is a repairing agent containing a filling component strong adherable to dental enamel when heated by laser beam irradiation.

4 Claims, 1 Drawing Sheet

METHOD FOR REPAIRING DENTAL ENAMEL

BACKGROUND OF THE INVENTION

1. Field of the Invention

The present invention relates to the repair of damage to dental enamel.

2. Description of the Prior Art

The surface of dental crowns in animals including humans is covered with enamel. The principal ingredient of enamel is calcium phosphate, specifically hydroxyapatite [$Ca_{10}(PO_4)_6(OH)_2$], enamel is the hardest among dental components and has greater protective functions against decayed teeth. Due to a variety of causes, however, damage to dental enamel occurs, for example caries, crack or wear. When such damage occurs, disorders such as decayed teeth may be triggered. Therefore, early repair of any damage to dental enamel is important for the maintenance of dental health.

It is significant for effective repair of dental enamel that a repairing agent with properties at the same or higher degree compared to those of dental enamel should adhere to the dental enamel as strongly as possible; most preferably, the repairing agent should adhere to the dental enamel at the same or greater strength compared to that of the dental enamel of itself. However, conventional therapeutic methods of repairing teeth do not provide these properties in a practical sense.

SUMMARY OF THE INVENTION

It is an objective of the present invention to provide a method for effectively repairing damage to dental enamel.

By the method of the present invention, by using a repairing agent containing a filling component capable of strong adhesion to dental enamel and heating the filling component contained in the repairing agent over laser irradiation, the filling component Is integrally sintered with the dental enamel for strong adhesion. More specifically, by applying to enamel damage a repairing agent containing a filling component adherable to dental enamel and irradiating laser onto the repairing agent, the filling component contained in the repairing agent is thus instantly heated to a higher temperature, whereby the filling component adheres to the enamel.

For the filling component in the repairing agent of dental enamel in accordance with the present invention, it is preferable to use a material having hardness and strength at the same or higher degree compared to those of dental enamel and having greater affinity for enamel with a resultant higher adhesiveness to the enamel. As material for such a component, artificial hydroxyapatite of the same composition as that of hydroxyapatite as the principal component of dental enamel will be preferable, and artificial hydroxyapatite in a ceramic preparation will be the most preferable.

So as to supplement the laser absorption ratio of the filling component, such as hydroxyapatite, it is preferable that the repairing agent of dental enamel for use in accordance with the present invention contains a laser absorption medium ingredient. By including such an absorption medium ingredient in the repairing agent, the heating efficiency of the laser can be enhanced, while simultaneously preventing the influence of the laser over the dental enamel. For such absorbing ingredient, a substance with a higher laser absorption coefficient can be used, including for example, carbon powder, metal powder or synthetic resin powder.

DETAILED DESCRIPTION OF THE PREFERRED EMBODIMENT

Figure 1:
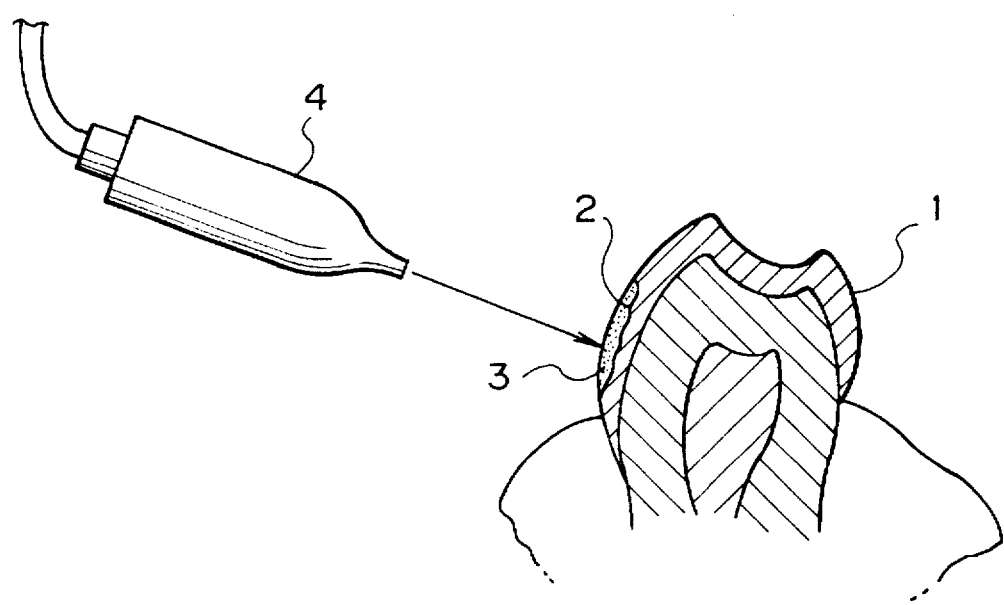
FIG. 1 is an explanatory view depicting a tooth in its repairing state of Example 1.

In carrying out the present invention in a preferable mode, the repairing agent for dental enamel should be comprised of a filling component of powdery hydroxyapatite $Ca_{10}(PO_4)_6(OH)_2$ prepared through bioceramic technology, to which filling component an appropriate amount of, for example, silver powder or carbon powder is mixed as an absorption medium ingredient, and water or the like is added to knead the mixture to become pasty.

In order to repair dental enamel using the paste, as shown in FIG. 1, damaged part 2 of dental enamel 1 is coated with enamel repairing agent 3. Then, pulsed laser beam of about 50 millijoule from a laser irradiating system 4 of Nd: YAG laser type is irradiated to the enamel repairing agent 3. The irradiated laser is absorbed into the enamel repairing agent 3, particularly through a laser absorbing ingredient contained in the agent, to instantly heat the enamel repairing agent 3 to a high temperature. While the absorbing ingredient is vaporized and drawn through the heating out of the enamel repairing agent 3, the hydroxyapatite, as the filling component, adheres to the enamel 1.

What is claimed is:

1. A method for repairing damaged dental enamel, said method comprising:
   (a) applying to the damaged enamel a repairing agent comprising
      (i) a filling component adherable to said dental enamel and
      (ii) an absorption medium ingredient said absorption medium ingredient showing high absorptivity to laser beam, and vaporizing when said filling component is subjected to laser;
   (b) irradiating the enamel repair agent with a laser, thereby adhering the enamel repairing agent to the enamel, and vaporizing and removing the absorbing ingredient.

2. The method of claim wherein the filling component is hydroxyapatite.

3. At The method of claim wherein the absorption medium is selected from the group consisting of carbon powder, metal powder and synthetic resin powder.

4. The method of claim 1 wherein the damage to dental enamel is selected from the group consisting of caries, cracks and wear.

* * * * *

UNITED STATES PATENT AND TRADEMARK OFFICE
CERTIFICATE OF CORRECTION

PATENT NO. : 5,752,833

DATED : May 19, 1998

INVENTOR(S) : Yamamoto

It is certified that error appears in the above-identified patent and that said Letters Patent is hereby corrected as shown below:

```
Claim 2, delete "The method of claim" insert therefor -- The
method of claim 1 --

Claim 3, delete "At The method of claim" insert therefor --
The method of claim 1 --
```

Signed and Sealed this

Twenty-fifth Day of August, 1998

Attest:

BRUCE LEHMAN

Attesting Officer

Commissioner of Patents and Trademarks